(12) United States Patent
Shelton, IV et al.

(10) Patent No.: US 8,083,120 B2
(45) Date of Patent: Dec. 27, 2011

(54) END EFFECTOR FOR USE WITH A SURGICAL CUTTING AND STAPLING INSTRUMENT

(75) Inventors: Frederick E. Shelton, IV, Hillsboro, OH (US); Richard F. Schwemberger, Cincinnati, OH (US); David C. Yates, West Chester, OH (US); Richard C. Smith, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 173 days.

(21) Appl. No.: 12/212,938

(22) Filed: Sep. 18, 2008

(65) Prior Publication Data

US 2010/0065605 A1 Mar. 18, 2010

(51) Int. Cl.
*A61B 17/68* (2006.01)
(52) U.S. Cl. ............ 227/180.1; 227/175.1; 227/176.1
(58) Field of Classification Search .... 227/175.1–182.1; 606/139, 219
See application file for complete search history.

(56) References Cited

U.S. PATENT DOCUMENTS

| | | | |
|---|---|---|---|
| 2,853,074 A | 9/1958 | Olson | |
| 3,551,987 A | 1/1971 | Wilkinson | |
| 4,429,695 A | 2/1984 | Green | |
| 4,506,671 A | 3/1985 | Green | |
| 4,619,262 A | 10/1986 | Taylor | |
| 4,809,695 A | 3/1989 | Gwathmey et al. | |
| 4,844,068 A | 7/1989 | Arata et al. | |
| 5,395,033 A * | 3/1995 | Byrne et al. | 227/175.1 |
| 5,405,072 A | 4/1995 | Zlock et al. | |
| 5,413,272 A | 5/1995 | Green et al. | |
| 5,417,361 A | 5/1995 | Williamson, IV | |
| 5,433,721 A * | 7/1995 | Hooven et al. | 606/143 |
| 5,480,089 A | 1/1996 | Blewett | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.

(Continued)

*Primary Examiner* — Paul Durand

(57) ABSTRACT

An end effector for a surgical cutting and stapling instrument. In various embodiments, the end effector may include an elongate channel that is configured to support a staple cartridge therein and which is also operably coupled to a surgical cutting and stapling instrument. An anvil may be movably supported relative to the elongate channel for selective movement between an open position and a closed position wherein tissue is clamped between the anvil and a staple cartridge supported within the elongate channel in response to a closing motion applied thereto from the surgical cutting and stapling instrument. At least one light source may be provided on at least one of the staple cartridge and the elongate channel. The light sources may interface with the anvil to provide a visual indication viewable through a portion of the anvil to indicate a position of tissue clamped between the anvil and the staple cartridge.

4 Claims, 11 Drawing Sheets

U.S. PATENT DOCUMENTS

| | | | |
|---|---|---|---|
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,711,472 A | 1/1998 | Bryan |
| 5,713,505 A | 2/1998 | Huitema |
| 5,715,987 A | 2/1998 | Kelley et al. |
| 5,718,360 A | 2/1998 | Green et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson IV et al. |
| 5,901,895 A | 5/1999 | Heaton et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,102,271 A | 8/2000 | Longo et al. |
| 6,119,913 A | 9/2000 | Adams et al. |
| 6,126,058 A | 10/2000 | Adams et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,629,630 B2 | 10/2003 | Adams |
| 6,644,532 B2 | 11/2003 | Green et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,755,338 B2 | 6/2004 | Hahnen et al. |
| 6,769,594 B2 | 8/2004 | Orban, III |
| 6,775,575 B2 * | 8/2004 | Bommannan et al. ........ 607/101 |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 * | 12/2005 | Shelton et al. ............. 227/176.1 |
| 6,978,922 B2 | 12/2005 | Bilotti et al. |
| 6,981,628 B2 | 1/2006 | Wales |
| 6,986,451 B1 | 1/2006 | Mastri et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |

| | | | | | |
|---|---|---|---|---|---|
| 7,207,471 B2 | 4/2007 | Heinrich et al. | 2005/0184121 A1 | 8/2005 | Heinrich |
| 7,207,472 B2 | 4/2007 | Wukusick et al. | 2005/0189397 A1 | 9/2005 | Jankowski |
| 7,210,609 B2 | 5/2007 | Leiboff et | 2005/0263563 A1 | 12/2005 | Racenet et al. |
| 7,213,736 B2 | 5/2007 | Wales et al. | 2005/0274768 A1 | 12/2005 | Cummins et al. |
| 7,225,964 B2 | 6/2007 | Mastri et al. | 2006/0011699 A1 | 1/2006 | Olson et al. |
| 7,234,624 B2 | 6/2007 | Gresham et al. | 2006/0049229 A1 | 3/2006 | Milliman et al. |
| 7,237,708 B1 | 7/2007 | Guy et al. | 2006/0108393 A1 | 5/2006 | Heinrich et al. |
| 7,258,262 B2 | 8/2007 | Mastri et al. | 2006/0180634 A1 | 8/2006 | Shelton, IV et al. |
| 7,278,562 B2 | 10/2007 | Mastri et al. | 2006/0226196 A1 | 10/2006 | Hueil et al. |
| 7,278,563 B1 | 10/2007 | Green | 2006/0273135 A1* | 12/2006 | Beetel ........................ 227/175.1 |
| 7,296,724 B2 | 11/2007 | Green et al. | 2006/0278680 A1 | 12/2006 | Viola et al. |
| 7,303,106 B2 | 12/2007 | Milliman et al. | 2006/0278681 A1 | 12/2006 | Viola et al. |
| 7,303,107 B2 | 12/2007 | Milliman et al. | 2006/0289602 A1 | 12/2006 | Wales et al. |
| 7,303,108 B2 | 12/2007 | Shelton, IV | 2007/0023476 A1 | 2/2007 | Whitman et al. |
| 7,328,828 B2 | 2/2008 | Ortiz et al. | 2007/0023477 A1 | 2/2007 | Whitman et al. |
| 7,328,829 B2 | 2/2008 | Arad et al. | 2007/0034668 A1 | 2/2007 | Holsten et al. |
| 7,354,447 B2 | 4/2008 | Shelton, IV et al. | 2007/0045379 A1 | 3/2007 | Shelton, IV |
| 7,364,060 B2 | 4/2008 | Milliman | 2007/0073340 A1 | 3/2007 | Shelton, IV et al. |
| 7,364,061 B2 | 4/2008 | Swayze et al. | 2007/0083234 A1 | 4/2007 | Shelton, IV et al. |
| 7,380,695 B2 | 6/2008 | Doll et al. | 2007/0084897 A1 | 4/2007 | Shelton, IV et al. |
| 7,380,696 B2 | 6/2008 | Shelton, IV et al. | 2007/0102452 A1 | 5/2007 | Shelton, IV et al. |
| 7,398,907 B2 | 7/2008 | Racenet et al. | 2007/0102453 A1 | 5/2007 | Morgan et al. |
| 7,398,908 B2 | 7/2008 | Holsten et al. | 2007/0102472 A1 | 5/2007 | Shelton, IV |
| 7,404,508 B2 | 7/2008 | Smith et al. | 2007/0102473 A1 | 5/2007 | Shelton, IV et al. |
| 7,404,509 B2 | 7/2008 | Ortiz et al. | 2007/0102474 A1 | 5/2007 | Shelton, IV et al. |
| 7,407,075 B2 | 8/2008 | Holsten et al. | 2007/0106317 A1 | 5/2007 | Shelton, IV et al. |
| 7,407,078 B2 | 8/2008 | Shelton, IV et al. | 2007/0114261 A1 | 5/2007 | Ortiz et al. |
| 7,410,086 B2 | 8/2008 | Ortiz et al. | 2007/0125826 A1* | 6/2007 | Shelton ........................ 227/175.1 |
| 7,416,101 B2 | 8/2008 | Shelton, IV et al. | 2007/0158385 A1 | 7/2007 | Hueil et al. |
| 7,419,080 B2 | 9/2008 | Smith et al. | 2007/0170225 A1 | 7/2007 | Shelton, IV et al. |
| 7,422,136 B1 | 9/2008 | Marczyk | 2007/0175949 A1 | 8/2007 | Shelton, IV et al. |
| 7,422,139 B2 | 9/2008 | Shelton, IV et al. | 2007/0175950 A1 | 8/2007 | Shelton, IV et al. |
| 7,424,965 B2 | 9/2008 | Racenet et al. | 2007/0175951 A1 | 8/2007 | Shelton, IV et al. |
| 7,431,188 B1 | 10/2008 | Marczyk | 2007/0175953 A1 | 8/2007 | Shelton, IV et al. |
| 7,431,189 B2 | 10/2008 | Shelton, IV et al. | 2007/0175955 A1 | 8/2007 | Shelton, IV et al. |
| 7,434,717 B2 | 10/2008 | Shelton, IV et al. | 2007/0175956 A1 | 8/2007 | Swayze et al. |
| 7,438,209 B1 | 10/2008 | Hess et al. | 2007/0175957 A1 | 8/2007 | Shelton, IV et al. |
| 7,441,684 B2 | 10/2008 | Shelton, IV et al. | 2007/0175958 A1 | 8/2007 | Shelton, IV et al. |
| 7,441,685 B1 | 10/2008 | Boudreaux | 2007/0175959 A1 | 8/2007 | Shelton, IV et al. |
| 7,448,525 B2 | 11/2008 | Shelton, IV et al. | 2007/0175960 A1 | 8/2007 | Shelton, IV et al. |
| 7,455,208 B2 | 11/2008 | Wales et al. | 2007/0175961 A1 | 8/2007 | Shelton, IV et al. |
| 7,481,347 B2 | 1/2009 | Roy | 2007/0175964 A1 | 8/2007 | Shelton, IV et al. |
| 7,494,039 B2 | 2/2009 | Racenet et al. | 2007/0179476 A1 | 8/2007 | Shelton, IV et al. |
| 7,506,790 B2 | 3/2009 | Shelton, IV | 2007/0181632 A1 | 8/2007 | Milliman |
| 7,510,107 B2 | 3/2009 | Timm et al. | 2007/0194079 A1 | 8/2007 | Hueil et al. |
| 7,546,940 B2 | 6/2009 | Milliman et al. | 2007/0194080 A1 | 8/2007 | Swayze et al. |
| 7,549,564 B2 | 6/2009 | Boudreaux | 2007/0194081 A1 | 8/2007 | Hueil et al. |
| 7,556,186 B2 | 7/2009 | Milliman | 2007/0194082 A1 | 8/2007 | Morgan et al. |
| 7,559,450 B2 | 7/2009 | Wales et al. | 2007/0221700 A1 | 9/2007 | Ortiz et al. |
| 7,575,144 B2 | 8/2009 | Ortiz et al. | 2007/0221701 A1 | 9/2007 | Ortiz et al. |
| 7,588,175 B2 | 9/2009 | Timm et al. | 2007/0225562 A1 | 9/2007 | Spivey et al. |
| 7,588,176 B2 | 9/2009 | Timm et al. | 2007/0233053 A1 | 10/2007 | Shelton, IV et al. |
| 7,597,229 B2 | 10/2009 | Boudreaux et al. | 2007/0246505 A1 | 10/2007 | Pace-Floridia et al. |
| 7,604,150 B2 | 10/2009 | Boudreaux | 2007/0262116 A1 | 11/2007 | Hueil et al. |
| 7,604,151 B2 | 10/2009 | Hess et al. | 2007/0295780 A1 | 12/2007 | Shelton et al. |
| 7,631,793 B2 | 12/2009 | Rethy et al. | 2008/0029570 A1 | 2/2008 | Shelton et al. |
| 7,658,311 B2 | 2/2010 | Boudreaux | 2008/0029573 A1 | 2/2008 | Shelton et al. |
| 7,665,646 B2 | 2/2010 | Prommersberger | 2008/0029574 A1 | 2/2008 | Shelton et al. |
| 7,669,747 B2 | 3/2010 | Weisenburgh, II et al. | 2008/0029575 A1 | 2/2008 | Shelton et al. |
| 7,673,782 B2 | 3/2010 | Hess et al. | 2008/0029576 A1 | 2/2008 | Shelton et al. |
| 7,699,204 B2 | 4/2010 | Viola | 2008/0029577 A1 | 2/2008 | Shelton et al. |
| 7,731,072 B2 | 6/2010 | Timm et al. | 2008/0035701 A1 | 2/2008 | Racenet et al. |
| 7,735,703 B2 | 6/2010 | Morgan et al. | 2008/0041917 A1 | 2/2008 | Racenet et al. |
| 7,743,960 B2 | 6/2010 | Whitman et al. | 2008/0078800 A1 | 4/2008 | Hess et al. |
| 7,753,245 B2 | 7/2010 | Boudreaux et al. | 2008/0078801 A1 | 4/2008 | Shelton et al. |
| 7,766,209 B2 | 8/2010 | Baxter, III et al. | 2008/0078802 A1 | 4/2008 | Hess et al. |
| 7,780,054 B2 | 8/2010 | Wales | 2008/0078803 A1 | 4/2008 | Shelton et al. |
| 7,784,662 B2 | 8/2010 | Wales et al. | 2008/0078804 A1 | 4/2008 | Shelton et al. |
| 7,793,812 B2 | 9/2010 | Moore et al. | 2008/0078805 A1 | 4/2008 | Omaits et al. |
| 7,798,386 B2 | 9/2010 | Schall et al. | 2008/0078806 A1 | 4/2008 | Omaits et al. |
| 2002/0117534 A1 | 8/2002 | Green et al. | 2008/0078807 A1 | 4/2008 | Hess et al. |
| 2004/0030231 A1* | 2/2004 | Norris ........................ 600/323 | 2008/0078808 A1 | 4/2008 | Hess et al. |
| 2004/0094597 A1 | 5/2004 | Whitman et al. | 2008/0082115 A1 | 4/2008 | Morgan et al. |
| 2004/0108357 A1 | 6/2004 | Milliman et al. | 2008/0082124 A1 | 4/2008 | Hess et al. |
| 2004/0164123 A1 | 8/2004 | Racenet et al. | 2008/0082125 A1 | 4/2008 | Murray et al. |
| 2004/0173659 A1 | 9/2004 | Green et al. | 2008/0082126 A1 | 4/2008 | Murray et al. |
| 2004/0222268 A1 | 11/2004 | Bilotti et al. | 2008/0083813 A1 | 4/2008 | Zemlok et al. |
| 2004/0232201 A1 | 11/2004 | Wenchell et al. | 2008/0164296 A1 | 7/2008 | Shelton et al. |
| 2005/0103819 A1 | 5/2005 | Racenet et al. | 2008/0167522 A1 | 7/2008 | Giordano et al. |

| | | |
|---|---|---|
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0001036 A1 | 1/2010 | Marczyk et al. |
| 2010/0032470 A1 | 2/2010 | Hess et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |

FOREIGN PATENT DOCUMENTS

| | | |
|---|---|---|
| CA | 2512960 A1 | 1/2006 |
| CA | 2514274 A1 | 1/2006 |
| CN | 1915180 A | 2/2007 |
| DE | 273689 C | 5/1914 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |

| | | | | | | |
|---|---|---|---|---|---|---|
| DE | 10314072 | A1 | 10/2004 | EP | 1256318 B1 | 5/2001 |
| DE | 202007003114 | U1 | 6/2007 | EP | 0806914 B1 | 9/2001 |
| EP | 0122046 | A1 | 10/1984 | EP | 0768840 B1 | 12/2001 |
| EP | 0070230 | B1 | 10/1985 | EP | 0908152 B1 | 1/2002 |
| EP | 0387980 | B1 | 10/1985 | EP | 0872213 B1 | 5/2002 |
| EP | 0033548 | B1 | 5/1986 | EP | 0862386 B1 | 6/2002 |
| EP | 0276104 | A2 | 7/1988 | EP | 0949886 B1 | 9/2002 |
| EP | 0248844 | B1 | 1/1993 | EP | 1238634 A2 | 9/2002 |
| EP | 0277959 | B1 | 10/1993 | EP | 0858295 B1 | 12/2002 |
| EP | 0233940 | B1 | 11/1993 | EP | 0656188 B1 | 1/2003 |
| EP | 0261230 | B1 | 11/1993 | EP | 1284120 A1 | 2/2003 |
| EP | 0639349 | A2 | 2/1994 | EP | 1287788 A1 | 3/2003 |
| EP | 0324636 | B1 | 3/1994 | EP | 0717966 B1 | 4/2003 |
| EP | 0593920 | A1 | 4/1994 | EP | 0869742 B1 | 5/2003 |
| EP | 0523174 | B1 | 6/1994 | EP | 0829235 B1 | 6/2003 |
| EP | 0600182 | A2 | 6/1994 | EP | 0887046 B1 | 7/2003 |
| EP | 0310431 | B1 | 11/1994 | EP | 0852480 B1 | 8/2003 |
| EP | 0375302 | B1 | 11/1994 | EP | 0891154 B1 | 9/2003 |
| EP | 0376562 | B1 | 11/1994 | EP | 0813843 B1 | 10/2003 |
| EP | 0630612 | A1 | 12/1994 | EP | 0873089 B1 | 10/2003 |
| EP | 0634144 | A1 | 1/1995 | EP | 0856326 B1 | 11/2003 |
| EP | 0646356 | A2 | 4/1995 | EP | 1374788 A1 | 1/2004 |
| EP | 0646357 | A1 | 4/1995 | EP | 0741996 B1 | 2/2004 |
| EP | 0653189 | A2 | 5/1995 | EP | 0814712 B1 | 2/2004 |
| EP | 0669104 | A1 | 8/1995 | EP | 1402837 A1 | 3/2004 |
| EP | 0511470 | B1 | 10/1995 | EP | 0705570 B1 | 4/2004 |
| EP | 0679367 | A2 | 11/1995 | EP | 0959784 B1 | 4/2004 |
| EP | 0392547 | B1 | 12/1995 | EP | 1407719 A2 | 4/2004 |
| EP | 0685204 | A1 | 12/1995 | EP | 1086713 B1 | 5/2004 |
| EP | 0364216 | B1 | 1/1996 | EP | 0996378 B1 | 6/2004 |
| EP | 0699418 | A1 | 3/1996 | EP | 1426012 A1 | 6/2004 |
| EP | 0702937 | A1 | 3/1996 | EP | 0833593 B2 | 7/2004 |
| EP | 0705571 | A1 | 4/1996 | EP | 1442694 A1 | 8/2004 |
| EP | 0711611 | A2 | 5/1996 | EP | 0888749 B1 | 9/2004 |
| EP | 0484677 | B2 | 6/1996 | EP | 0959786 B1 | 9/2004 |
| EP | 0541987 | B1 | 7/1996 | EP | 1459695 A1 | 9/2004 |
| EP | 0667119 | B1 | 7/1996 | EP | 1473819 A1 | 11/2004 |
| EP | 0708618 | B1 | 3/1997 | EP | 1477119 A1 | 11/2004 |
| EP | 0770355 | A1 | 5/1997 | EP | 1479345 A1 | 11/2004 |
| EP | 0503662 | B1 | 6/1997 | EP | 1479347 A1 | 11/2004 |
| EP | 0447121 | B1 | 7/1997 | EP | 1479348 A1 | 11/2004 |
| EP | 0625077 | B1 | 7/1997 | EP | 0754437 B2 | 12/2004 |
| EP | 0633749 | B1 | 8/1997 | EP | 1025807 B1 | 12/2004 |
| EP | 0710090 | B1 | 8/1997 | EP | 1001710 B1 | 1/2005 |
| EP | 0578425 | B1 | 9/1997 | EP | 1520521 A1 | 4/2005 |
| EP | 0625335 | B1 | 11/1997 | EP | 1520523 A1 | 4/2005 |
| EP | 0552423 | B1 | 1/1998 | EP | 1520525 A1 | 4/2005 |
| EP | 0592244 | B1 | 1/1998 | EP | 1522264 A1 | 4/2005 |
| EP | 0648476 | B1 | 1/1998 | EP | 1523942 A2 | 4/2005 |
| EP | 0649290 | B1 | 3/1998 | EP | 1550408 A1 | 7/2005 |
| EP | 0598618 | B1 | 9/1998 | EP | 1557129 A1 | 7/2005 |
| EP | 0676173 | B1 | 9/1998 | EP | 1064883 B1 | 8/2005 |
| EP | 0678007 | B1 | 9/1998 | EP | 1067876 B1 | 8/2005 |
| EP | 0603472 | B1 | 11/1998 | EP | 0870473 B1 | 9/2005 |
| EP | 0605351 | B1 | 11/1998 | EP | 1157666 B1 | 9/2005 |
| EP | 0878169 | A1 | 11/1998 | EP | 0880338 B1 | 10/2005 |
| EP | 0879742 | A1 | 11/1998 | EP | 1158917 B1 | 11/2005 |
| EP | 0695144 | B1 | 12/1998 | EP | 1344498 B1 | 11/2005 |
| EP | 0722296 | B1 | 12/1998 | EP | 1330989 B1 | 12/2005 |
| EP | 0760230 | B1 | 2/1999 | EP | 0771176 B2 | 1/2006 |
| EP | 0623316 | B1 | 3/1999 | EP | 1621138 A2 | 2/2006 |
| EP | 0650701 | B1 | 3/1999 | EP | 1621139 A2 | 2/2006 |
| EP | 0537572 | B1 | 6/1999 | EP | 1621141 A2 | 2/2006 |
| EP | 0923907 | A1 | 6/1999 | EP | 1621145 A2 | 2/2006 |
| EP | 0843906 | B1 | 3/2000 | EP | 1621151 A2 | 2/2006 |
| EP | 0552050 | B1 | 5/2000 | EP | 1034746 B1 | 3/2006 |
| EP | 0833592 | B1 | 5/2000 | EP | 1632191 A2 | 3/2006 |
| EP | 0830094 | B1 | 9/2000 | EP | 1065981 B1 | 5/2006 |
| EP | 1034747 | A1 | 9/2000 | EP | 1082944 B1 | 5/2006 |
| EP | 1034748 | A1 | 9/2000 | EP | 1652481 A2 | 5/2006 |
| EP | 0694290 | B1 | 11/2000 | EP | 1382303 B1 | 6/2006 |
| EP | 1050278 | A1 | 11/2000 | EP | 1253866 B1 | 7/2006 |
| EP | 1053719 | A1 | 11/2000 | EP | 1032318 B1 | 8/2006 |
| EP | 1053720 | A1 | 11/2000 | EP | 1045672 B1 | 8/2006 |
| EP | 1055399 | A1 | 11/2000 | EP | 1617768 B1 | 8/2006 |
| EP | 1055400 | A1 | 11/2000 | EP | 1693015 A2 | 8/2006 |
| EP | 1080694 | A1 | 3/2001 | EP | 1400214 B1 | 9/2006 |
| EP | 1090592 | A1 | 4/2001 | EP | 1702567 A2 | 9/2006 |
| EP | 1095627 | A1 | 5/2001 | EP | 1129665 B1 | 11/2006 |

| | | | | | | |
|---|---|---|---|---|---|---|
| EP | 1400206 | B1 | 11/2006 | RU | 2225170 C2 | 3/2004 |
| EP | 1256317 | B1 | 12/2006 | SU | 886900 A1 | 12/1981 |
| EP | 1728473 | A1 | 12/2006 | SU | 1377053 A1 | 2/1988 |
| EP | 1728475 | A2 | 12/2006 | SU | 1561964 A1 | 5/1990 |
| EP | 1479346 | B1 | 1/2007 | SU | 1722476 A1 | 3/1992 |
| EP | 1484024 | B1 | 1/2007 | WO | WO 91/15157 A1 | 10/1991 |
| EP | 1754445 | A2 | 2/2007 | WO | WO 92/21300 A1 | 12/1992 |
| EP | 1759812 | A1 | 3/2007 | WO | WO 93/08755 A1 | 5/1993 |
| EP | 1767163 | A1 | 3/2007 | WO | WO 93/13718 A1 | 7/1993 |
| EP | 1769756 | A1 | 4/2007 | WO | WO 93/14690 A1 | 8/1993 |
| EP | 1769758 | A1 | 4/2007 | WO | WO 93/15850 A1 | 8/1993 |
| EP | 1581128 | B1 | 5/2007 | WO | WO 93/19681 A1 | 10/1993 |
| EP | 1785097 | A2 | 5/2007 | WO | WO 94/00060 A1 | 1/1994 |
| EP | 1790293 | A2 | 5/2007 | WO | WO 94/11057 A1 | 5/1994 |
| EP | 1800610 | A1 | 6/2007 | WO | WO 94/12108 A1 | 6/1994 |
| EP | 1300117 | B1 | 8/2007 | WO | WO 94/18893 A1 | 9/1994 |
| EP | 1813199 | A1 | 8/2007 | WO | WO 94/22378 A1 | 10/1994 |
| EP | 1813201 | A1 | 8/2007 | WO | WO 94/23659 A1 | 10/1994 |
| EP | 1813203 | A2 | 8/2007 | WO | WO 95/02369 A1 | 1/1995 |
| EP | 1813207 | A1 | 8/2007 | WO | WO 95/03743 A1 | 2/1995 |
| EP | 1813209 | A1 | 8/2007 | WO | WO 95/06817 A1 | 3/1995 |
| EP | 1487359 | B1 | 10/2007 | WO | WO 95/09576 A1 | 4/1995 |
| EP | 1599146 | B1 | 10/2007 | WO | WO 95/09577 A1 | 4/1995 |
| EP | 1839596 | A1 | 10/2007 | WO | WO 95/14436 A1 | 6/1995 |
| EP | 1402821 | B1 | 12/2007 | WO | WO 95/17855 A1 | 7/1995 |
| EP | 1872727 | A1 | 1/2008 | WO | WO 95/18383 A1 | 7/1995 |
| EP | 1897502 | A1 | 3/2008 | WO | WO 95/18572 A1 | 7/1995 |
| EP | 1330201 | B1 | 6/2008 | WO | WO 95/19739 A1 | 7/1995 |
| EP | 1702568 | B1 | 7/2008 | WO | WO 95/20360 A1 | 8/1995 |
| EP | 1943976 | A2 | 7/2008 | WO | WO 95/23557 A1 | 9/1995 |
| EP | 1593337 | B1 | 8/2008 | WO | WO 95/24865 A1 | 9/1995 |
| EP | 1970014 | A1 | 9/2008 | WO | WO 95/25471 A3 | 9/1995 |
| EP | 1980213 | A2 | 10/2008 | WO | WO 95/26562 A1 | 10/1995 |
| EP | 1759645 | B1 | 11/2008 | WO | WO 95/29639 A1 | 11/1995 |
| EP | 1693008 | B1 | 12/2008 | WO | WO 96/04858 A1 | 2/1996 |
| EP | 1759640 | B1 | 12/2008 | WO | WO 96/19151 A1 | 6/1996 |
| EP | 2000102 | A2 | 12/2008 | WO | WO 96/19152 A1 | 6/1996 |
| EP | 1749486 | B1 | 3/2009 | WO | WO 96/20652 A1 | 7/1996 |
| EP | 1721576 | B1 | 4/2009 | WO | WO 96/21119 A1 | 7/1996 |
| EP | 2090256 | A2 | 8/2009 | WO | WO 96/22055 A1 | 7/1996 |
| EP | 1607050 | B1 | 12/2009 | WO | WO 96/23448 A1 | 8/1996 |
| EP | 1566150 | B1 | 4/2010 | WO | WO 96/24301 A1 | 8/1996 |
| EP | 1813206 | B1 | 4/2010 | WO | WO 96/27337 A1 | 9/1996 |
| EP | 1769754 | B1 | 6/2010 | WO | WO 96/35464 A1 | 11/1996 |
| EP | 1535565 | B1 | 10/2010 | WO | WO 96/39085 A1 | 12/1996 |
| EP | 1702570 | B1 | 10/2010 | WO | WO 96/39086 A1 | 12/1996 |
| FR | 999646 | A | 2/1952 | WO | WO 96/39087 A1 | 12/1996 |
| FR | 1112936 | A | 3/1956 | WO | WO 96/39088 A1 | 12/1996 |
| FR | 2765794 | A | 1/1999 | WO | WO 96/39089 A1 | 12/1996 |
| GB | 939929 | A | 10/1963 | WO | WO 97/00646 A1 | 1/1997 |
| GB | 1210522 | A | 10/1970 | WO | WO 97/00647 A1 | 1/1997 |
| GB | 1217159 | A | 12/1970 | WO | WO 97/06582 A1 | 2/1997 |
| GB | 2109241 | A | 6/1983 | WO | WO 97/10763 A1 | 3/1997 |
| GB | 2272159 | A | 5/1994 | WO | WO 97/10764 A1 | 3/1997 |
| GB | 2284242 | A | 5/1995 | WO | WO 97/11648 A2 | 4/1997 |
| GB | 2336214 | A | 10/1999 | WO | WO 97/11649 A1 | 4/1997 |
| GB | 2425903 | A | 11/2006 | WO | WO 97/15237 A1 | 5/1997 |
| JP | 6007357 | A | 1/1994 | WO | WO 97/24073 A1 | 7/1997 |
| JP | 7051273 | A | 2/1995 | WO | WO 97/24993 A1 | 7/1997 |
| JP | 8033641 | A | 2/1996 | WO | WO 97/30644 A1 | 8/1997 |
| JP | 8229050 | A | 9/1996 | WO | WO 97/34533 A1 | 9/1997 |
| JP | 2000033071 | A | 2/2000 | WO | WO 97/37598 A1 | 10/1997 |
| JP | 2000171730 | A | 6/2000 | WO | WO 97/39688 A2 | 10/1997 |
| JP | 2000287987 | A | 10/2000 | WO | WO 98/17180 A1 | 4/1998 |
| JP | 2000325303 | A | 11/2000 | WO | WO 98/27880 A1 | 7/1998 |
| JP | 2001286477 | A | 10/2001 | WO | WO 98/30153 A1 | 7/1998 |
| JP | 2002143078 | A | 5/2002 | WO | WO 98/47436 A1 | 10/1998 |
| JP | 2002369820 | A | 12/2002 | WO | WO 99/03407 A1 | 1/1999 |
| JP | 2005505322 | T | 2/2005 | WO | WO 99/03408 A1 | 1/1999 |
| JP | 2005103293 | A | 4/2005 | WO | WO 99/03409 A1 | 1/1999 |
| JP | 2005131163 | A | 5/2005 | WO | WO 99/12483 A1 | 3/1999 |
| JP | 2005131164 | A | 5/2005 | WO | WO 99/12487 A1 | 3/1999 |
| JP | 2005131173 | A | 5/2005 | WO | WO 99/12488 A1 | 3/1999 |
| JP | 2005131211 | A | 5/2005 | WO | WO 99/15086 A1 | 4/1999 |
| JP | 2005131212 | A | 5/2005 | WO | WO 99/15091 A1 | 4/1999 |
| JP | 2005137423 | A | 6/2005 | WO | WO 99/23933 A2 | 5/1999 |
| JP | 2005152416 | A | 6/2005 | WO | WO 99/23959 A1 | 5/1999 |
| JP | 2006-281405 | A | 10/2006 | WO | WO 99/25261 A1 | 5/1999 |
| RU | 2187249 | C2 | 8/2002 | WO | WO 99/29244 A1 | 6/1999 |

| | | | |
|---|---|---|---|
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

European Search Report, Application No. 09252214.3, dated Jan. 25, 2010 (4 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

* cited by examiner

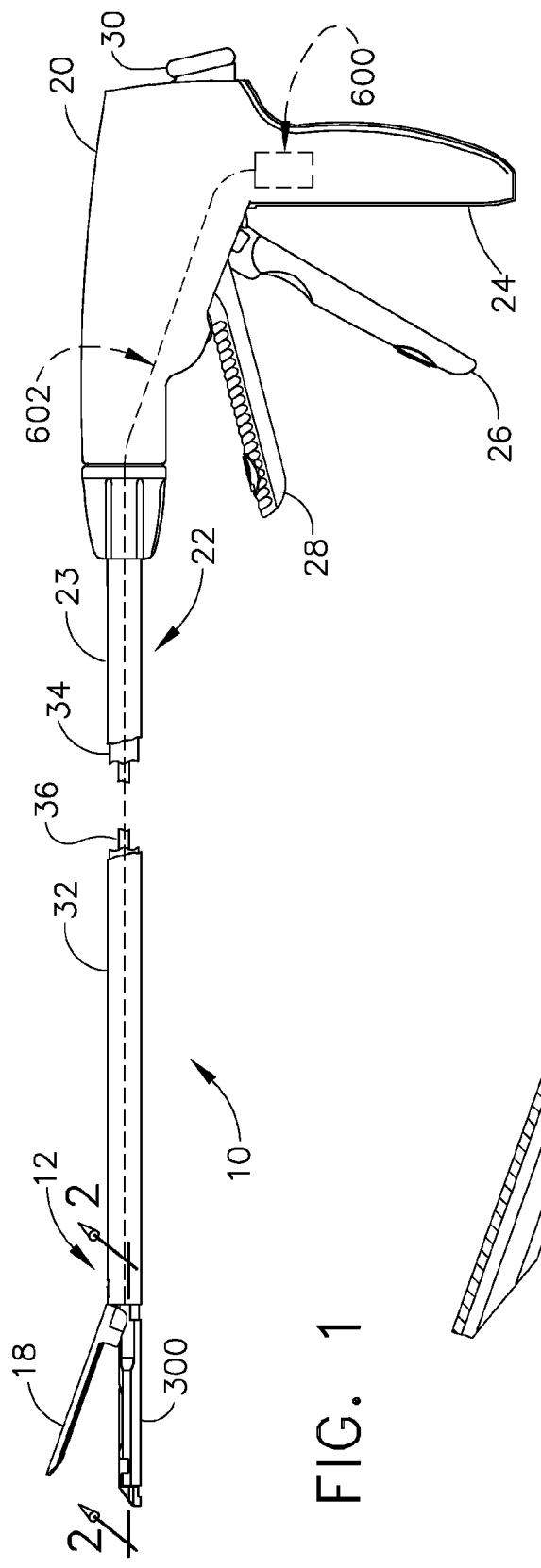
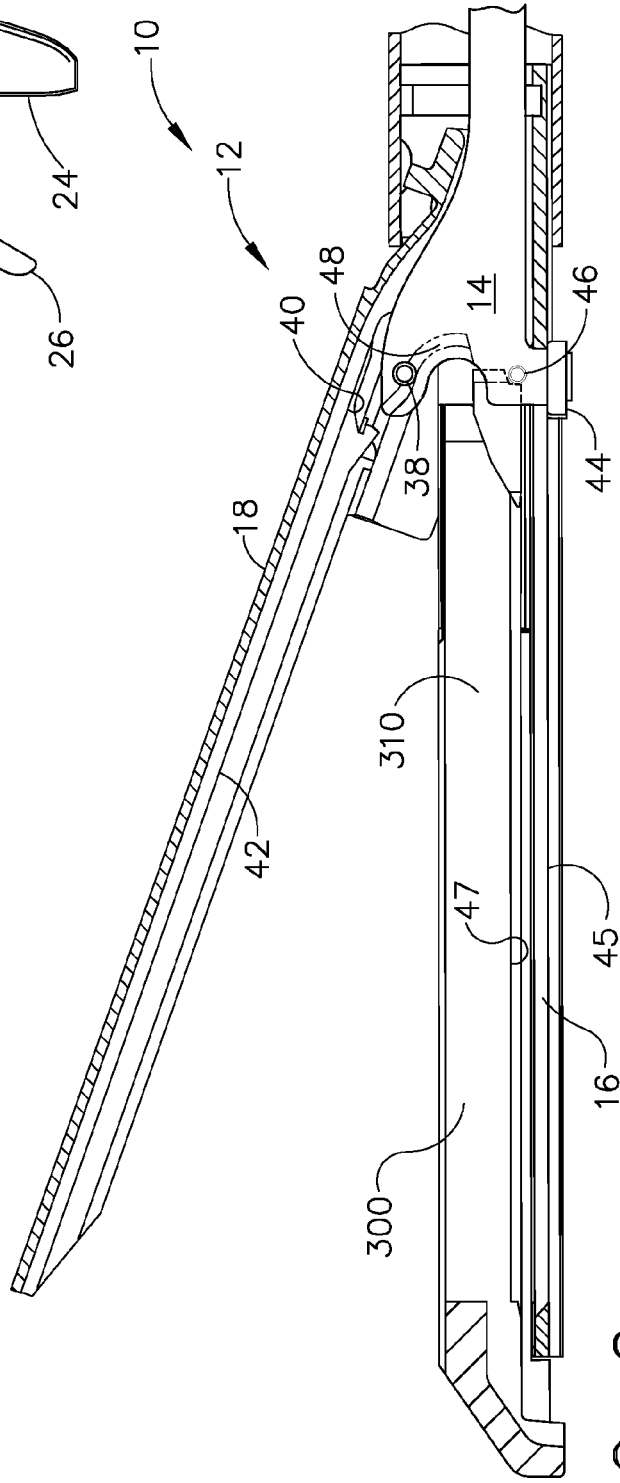
FIG. 1
FIG. 2

END EFFECTOR FOR USE WITH A SURGICAL CUTTING AND STAPLING INSTRUMENT

FIELD OF THE INVENTION

The present invention relates in general to endoscopic surgical instruments that are capable of manipulating tissue and applying lines of staples to tissue while cutting the tissue between those staple lines and, more particularly, to improvements relating to end effectors for such instruments.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members is configured to receive a staple cartridge equipped with laterally spaced rows of staples. The other jaw member commonly comprises an anvil that has staple-forming pockets formed therein that are aligned with the rows of staples in the cartridge. Various cartridges have wedges that, when driven distally through the cartridge, engage drivers upon which the staples are supported to effect the firing of the staples toward the anvil.

In use, a clinician opens and closes the jaw members of the stapler to position and clamp the tissue therein prior to firing. Once the clinician has determined that tissue is properly clamped in the jaw members, the instrument is activated or "fired" to thereby cut and simultaneously staple the tissue on each side of the cut. The simultaneous severing and stapling avoids complications that may arise when performing such actions sequentially with different surgical tools that respectively only cut or staple.

When employing such cutting and severing instruments, however, the clinician must properly position the tissue to be cut within the end effector before firing the device. This task may be complicated due to the location of the tissue and/or the position of the end effector within the body cavity.

Consequently, a significant need exists for an improved end effector that is configured to provide the clinician with an indication of the position of the tissue within the end effector.

BRIEF SUMMARY OF THE INVENTION

In accordance with various embodiments of the present invention, there is a provided an end effector for a surgical cutting and stapling instrument. The end effector may comprise an elongate channel that is configured to support a staple cartridge therein and which is operably coupled to the surgical cutting and stapling instrument. An anvil may be movably supported relative to the elongate channel for selective movement between open and closed positions. Tissue may be clamped between the anvil and a staple cartridge supported within the elongate channel in response to a closing motion applied thereto from the surgical cutting and stapling instrument. At least one light source may be provided on at least one of the staple cartridge and the elongate channel. The light sources may be arranged to interface with the anvil to provide a visual indication of the tissue's position between the anvil and the staple cartridge.

In accordance with another embodiment of the present invention, there is provided a staple cartridge for use with a surgical cutting and stapling instrument. In various embodiments, the staple cartridge may comprise a cartridge body that has a plurality of staple-receiving channels therein. Each staple-receiving channel may operably support at least one surgical staple therein. A plurality of light sources may be supported within the cartridge body for projecting light towards an anvil portion of the surgical cutting and stapling instrument when the staple cartridge is operably supported therein and the anvil portion is oriented in a tissue clamping position.

In accordance with another embodiment of the present invention, there is provided a staple cartridge for use with a surgical cutting and stapling instrument that has at least one source of light therein. Various embodiments may comprise a cartridge body that has a plurality of staple-receiving channels therein. Each staple-receiving channel may operably support at least one surgical staple therein. A plurality of light-projecting openings may extend through the cartridge body in such positions as to project light from the light source towards an anvil portion of the surgical cutting and stapling instrument when the staple cartridge is operably supported therein and the anvil portion is oriented in a tissue clamping position.

In accordance with another embodiment of the present invention, there is provided a surgical cutting and stapling instrument that may include a handle assembly and an elongate shaft that is operably coupled to the handle assembly. An elongate channel may be operably coupled to the elongate shaft and may be configured to operably support a staple cartridge therein. An anvil may be movably supported relative to the elongate channel for selective movement between an open position and a closed position wherein tissue is clamped between the anvil and a staple cartridge supported within the elongate channel in response to opening and closing motions applied thereto from the elongate shaft. At least one light source may be provided on at least one of the staple cartridge and the elongate channel. The light sources interface with the anvil to provide a visual indication viewable through a portion of the anvil to indicate a position of tissue clamped between the anvil and the staple cartridge.

Accordingly, various embodiments of the invention provide solutions to the shortcomings of other end effectors used to clamp and/or manipulate tissue as well as those end effectors designed to cut and staple tissue. Those of ordinary skill in the art will readily appreciate, however, that these and other details, features and advantages will become further apparent as the following detailed description proceeds.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 depicts a partially cut away side elevation view of a surgical cutting and stapling instrument of an embodiment of the present invention in an open position.

FIG. 2 depicts a cross-sectional side elevation detail view along the line 2-2 of FIG. 1 of the end effector thereof.

DETAILED DESCRIPTION OF THE INVENTION

Figure 3:
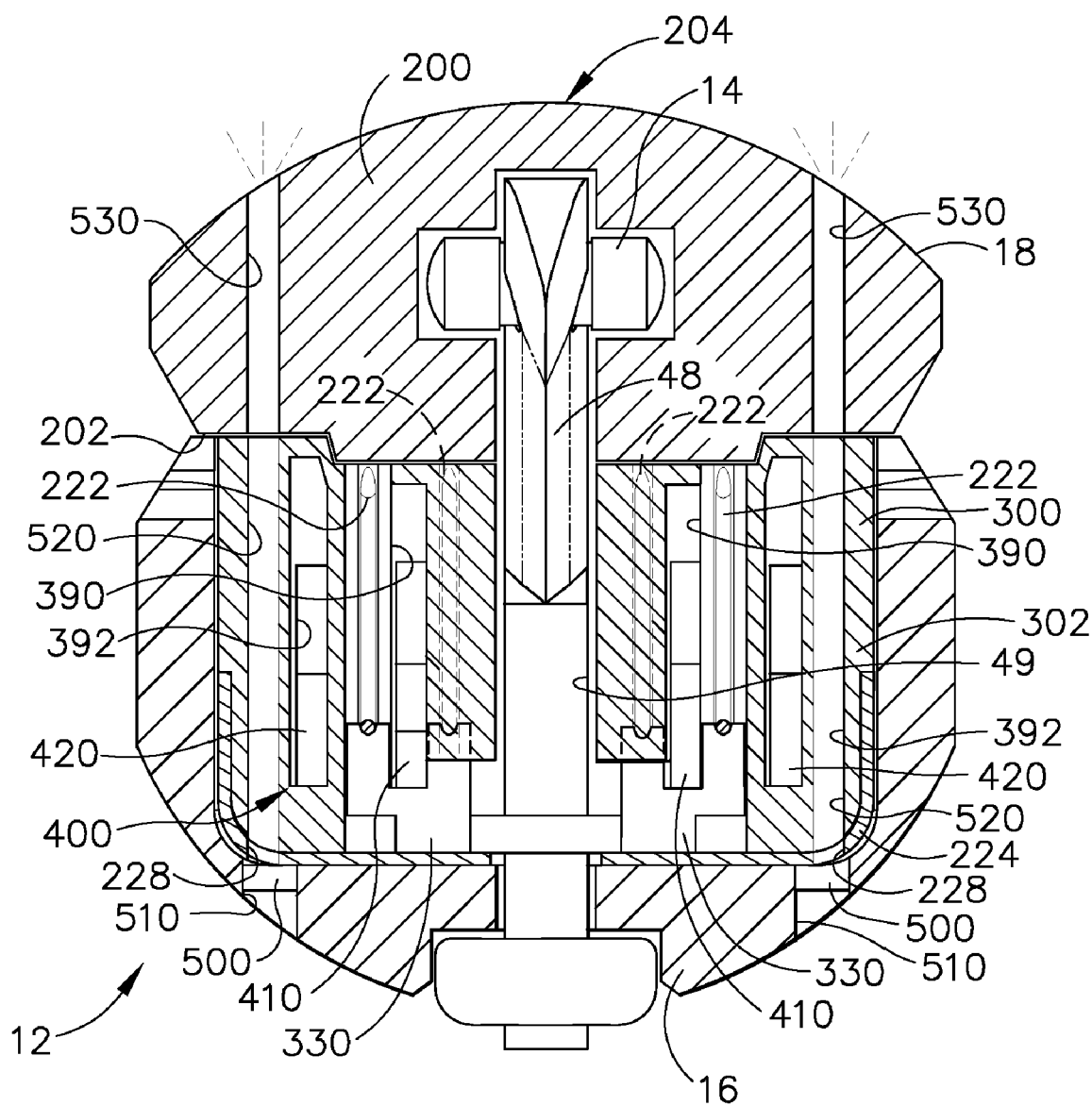
FIG. 3 is a cross-sectional view of the end effector of FIG. 2 with the anvil thereof in a closed position.

Turning to the Drawings, wherein like numerals denote like components throughout the several views, FIGS. 1 and 2 depict one embodiment of a surgical stapling and severing instrument 10 that is capable of practicing the unique benefits of the present invention. As the present Detailed Description proceeds, the reader will appreciate, however, that the unique and novel aspects of the present invention may be advantageously employed in connection with a variety of other staplers, stapler instruments and even tissue grasping instruments without departing from the spirit and scope of the present invention. Accordingly, the scope of protection afforded to the various embodiments of the present invention should not be limited to use only with the specific type of surgical cutting and stapling instruments described herein.

FIGS. 1 and 2, illustrate one form of a surgical cutting and stapling instrument, generally designated as 10 that may be effectively employed in connection with various embodiments of the present invention. As can be seen from those Figures, the surgical cutting and stapling instrument 10 may includes a handle assembly 20 that is connected to an implement portion 22, the latter further comprising an elongate shaft 23 distally terminating in an end effector 12. The handle assembly 20 may include a pistol grip 24 toward which a closure trigger 26 may be pivotally drawn by the clinician to cause clamping, or closing, of an anvil 18 toward an elongate channel 16 of the end effector 12. A firing trigger 28 may be operably mounted farther outboard of the closure trigger 26 and may be pivotally drawn by the clinician to cause the stapling and severing of tissue clamped in the end effector 12.

It will be appreciated that the terms "proximal" and "distal" are used herein with reference to a clinician gripping a handle of an instrument. Thus, the end effector 12 is distal with respect to the more proximal handle assembly 20. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Various embodiments of the instrument 10 may also include a closure sleeve 32 that is movably mounted on a frame 34. The frame 34 may enclose a firing drive member 36 that is actuated by the firing trigger 28. The frame 34 connects the handle assembly 20 to the end effector 12. In particular, the distal end of the frame 34 is coupled to the elongate channel 16 of the end effector 12 which may be configured to removably support a staple cartridge 300.

As can be seen in FIG. 3, the staple cartridge 300 has an elongate vertical slot 49 extending therethrough to enable the firing bar 14 to pass therethrough. The firing bar 14 has a cutting edge 48 thereon for severing the clamped tissue. Various types and configurations of firing bars are known. For example, those firing bars disclosed in U.S. Pat. No. 6,978,921, issued on Dec. 27, 2005, the disclosure of which is herein incorporated by reference in its entirety, may be effectively employed. However, the surgical cutting and stapling instrument 10 may also use other firing bar arrangements.

With reference to FIGS. 4-7, the handle assembly 20 may consist of first and second base sections 50 and 52, which may bee molded from a polymeric material such as a glass-filled polycarbonate. The first base section 50 may be provided with a plurality of cylindrically-shaped pins 54. The second base section 52 may include a plurality of extending members 56, each having a hexagonal-shaped opening 58. The cylindrically-shaped pins 54 may be received within the hexagonal-shaped openings 58 and be frictionally held therein for maintaining the first and second base sections 50 and 52 in assembly.

Various embodiments may also include a rotating knob 60 that has a bore 62 extending completely through it for engaging and rotating the implement portion 22 about its longitudinal axis. The rotating knob 60 may include an inwardly protruding boss 64 that extends along at least a portion of the bore 62. The protruding boss 64 may be received within a longitudinal slot 66 formed at a proximal portion of the closure sleeve 32 such that rotation of the rotating knob 60 effects rotation of the closure sleeve 32. The boss 64 may further extend through frame 34 into contact with a portion of the firing drive member 36 to effect their rotation as well. Thus, the end effector 12 (not shown in FIGS. 4-7) may be rotated with the rotating knob 60.

A proximal end 68 of the frame 34 may pass proximally through the rotating knob 60 and may further have a circumferential notch 70 that is engaged by opposing channel securement members 72 extending respectively from the base sections 50 and 52. Only the channel securement member 72 of the second base section 52 is shown. The channel securement members 72, extending from the base sections 50, 52 serve to secure the frame 34 to the handle assembly 20 such that the frame 34 does not move longitudinally relative to the handle assembly 20.

The closure trigger 26 may have a handle section 74, a gear segment section 76, and an intermediate section 78. A bore 80 may extend through the intermediate section 78. A cylindrical support member 82 may extend from the second base section 52 and pass through the bore 80 for pivotably mounting the closure trigger 26 on the handle assembly 20. A second cylindrical support member 83 extending from the second base section 52 may pass through a bore 81 of firing trigger 28 for pivotally mounting on the handle assembly 20. A hexagonal opening 84 may be provided in the cylindrical support member 83 for receiving a securement pin (not shown) that extends from the first base section 50.

A closure yoke 86 may be housed within the handle assembly 20 for reciprocating movement therein and may serve to transfer motion from the closure trigger 26 to the closure sleeve 32. Support members 88 extending from the second base section 52 and securement member 72, which extends through a recess 89 in the yoke 86, may support the yoke 86 within the handle assembly 20. A proximal end 90 of the closure sleeve 32 may be provided with a flange 92 that is snap-fitted into a receiving recess 94 formed in a distal end 96 of the yoke 86. A proximal end 98 of the yoke 86 may have a gear rack 100 that is engaged by the gear segment section 76 of the closure trigger 26. When the closure trigger 26 is moved toward the pistol grip 24 of the handle assembly 20, the yoke 86 and, hence, the closure sleeve 32 move distally, compressing a spring 102 that biases the yoke 86 proximally. Distal movement of the closure sleeve 32 effects pivotal translation movement of the anvil 18 toward the elongate channel 16 of the end effector 12 and proximal movement effects opening, as discussed below.

The closure trigger 26 may be forward biased to an open position by a front surface 130 interacting with an engaging surface 128 of the firing trigger 28. A first hook 104 that pivots top to rear in the handle assembly 20 about a pin 106 may restrain movement of the firing trigger 28 toward the pistol grip 24 until the closure trigger 26 is clamped to its closed position. Hook 104 may restrain firing trigger 28 motion by engaging a lockout pin 107 in firing trigger 28. The hook 104 may also be in contact with the closure trigger 26. In particular, a forward projection 108 of the hook 104 may engage a member 110 on the intermediate section 78 of the closure trigger 26, the member 100 being outward of the bore 80 toward the handle section 74. Hook 104 may be biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 6:
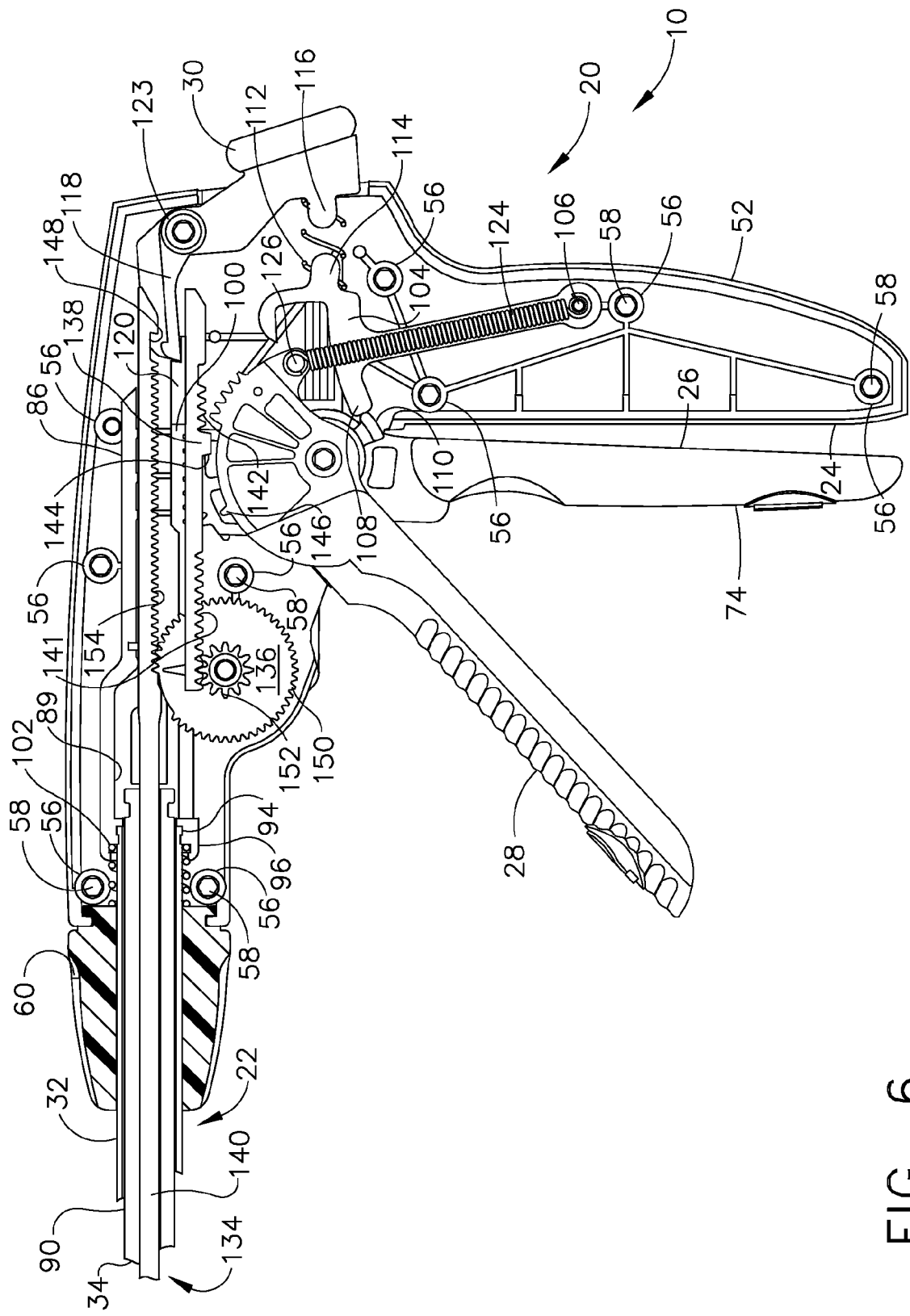
FIG. 6 depicts a side elevational view of the handle portion of the proximal end of the surgical cutting and stapling instrument of FIG. 1 with the left side removed to expose interior parts in the closed ("clamped") position.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 6.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26. A firing trigger return spring 124 may be located within the handle assembly 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 may be located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 may extend from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIGS. 4-7) and a metal drive rod 140. The drive member 138 may include first and second gear racks 141 and 142. A first notch 144 may be provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 may be located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 may be engaged with a first gear rack 154 provided on the metal drive rod 140. The second integral pinion gear 152 may be engaged with the first gear rack 141 on the drive member 138. The first integral pinion gear 150 may have a first diameter and the second integral pinion gear 152 may have a second diameter which is smaller than the first diameter.

Figure 4:
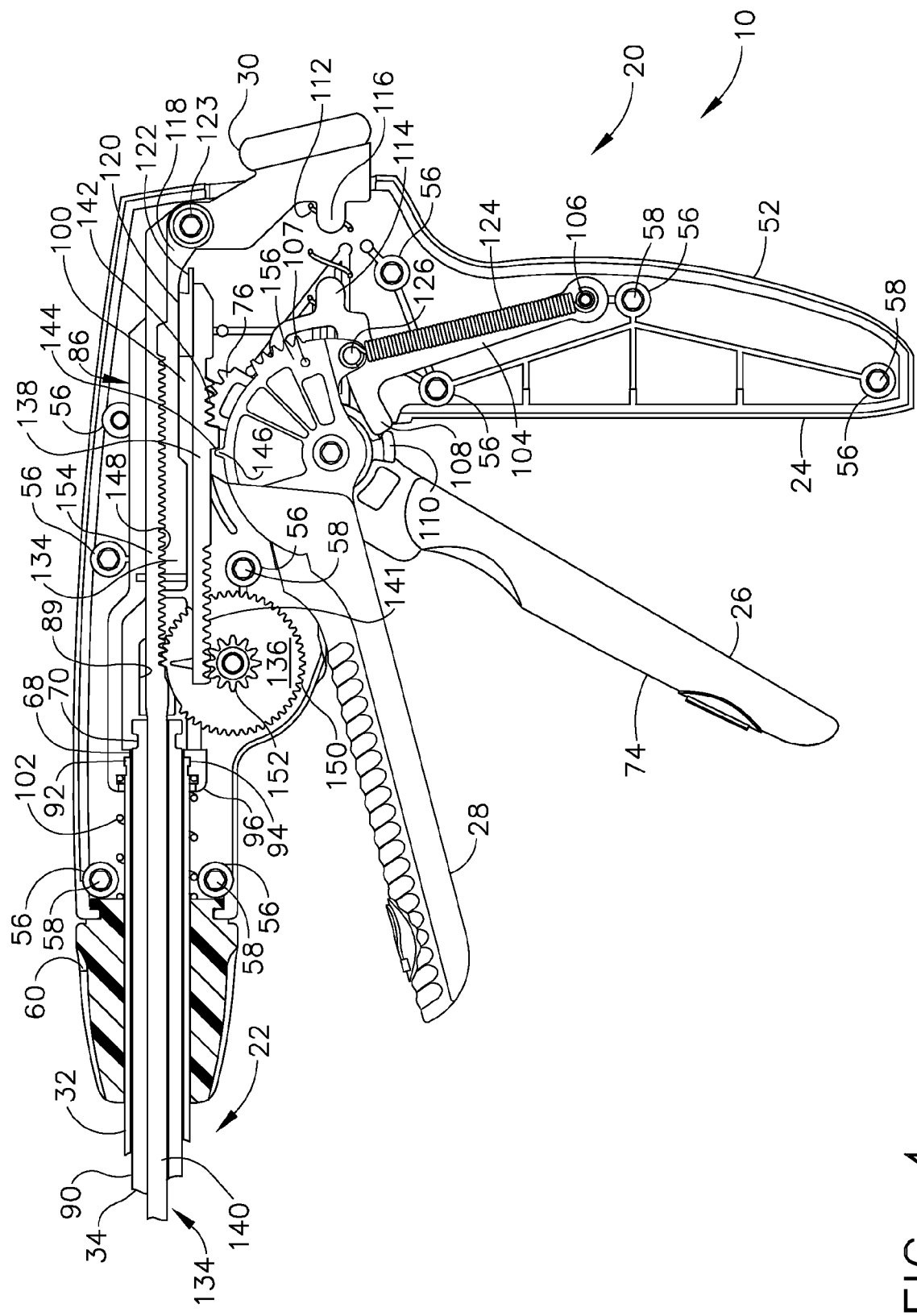
FIG. 4 depicts a side elevational view of a handle portion of a proximal end of the surgical cutting and stapling instrument of FIG. 1 with a left side removed to expose interior parts in an unclamped, unfired ("start") position.
Figure 5:
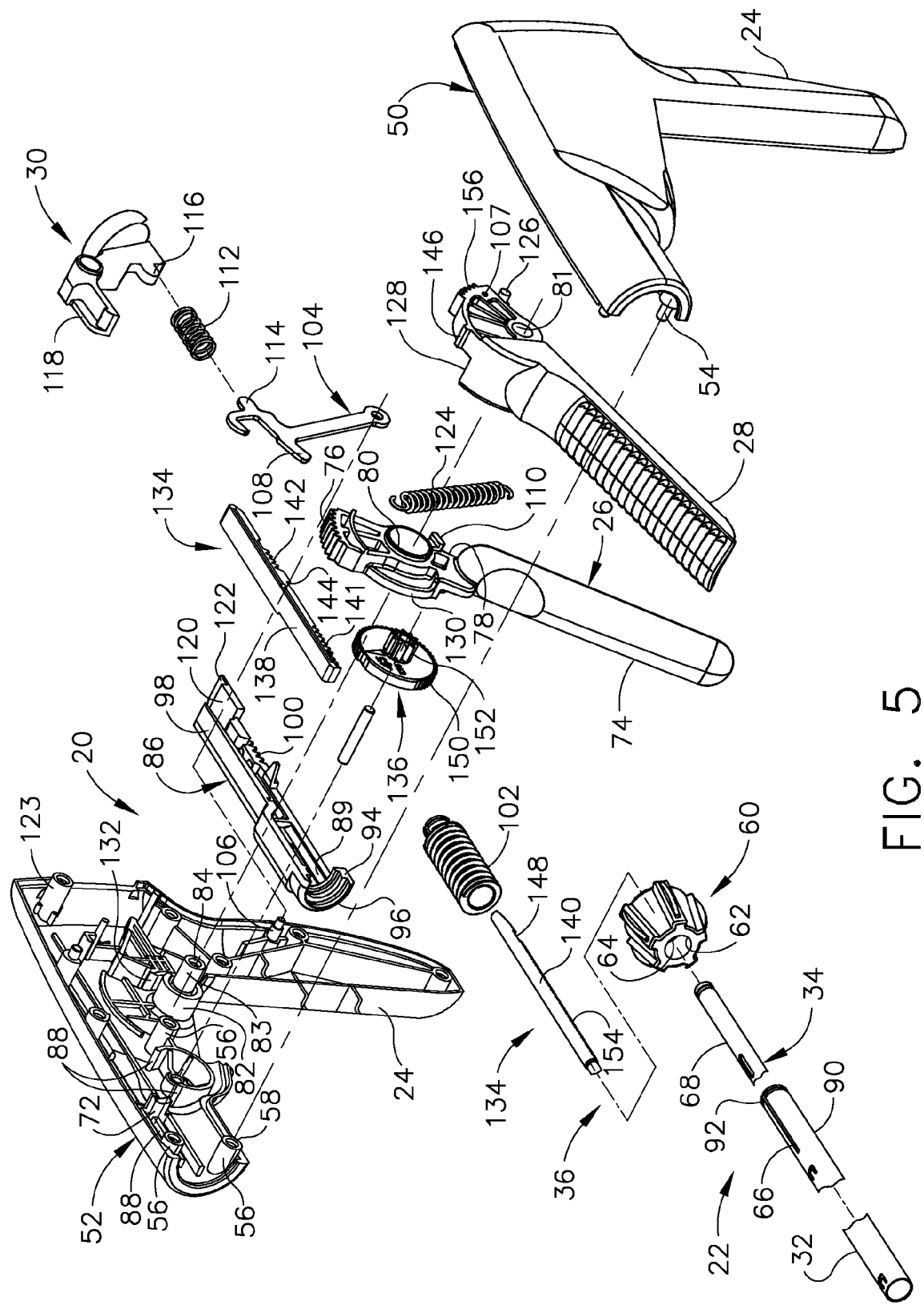
FIG. 5 depicts a perspective, exploded view of the handle portion of the proximal end of the surgical cutting and stapling instrument of FIG. 1.
Figure 7:
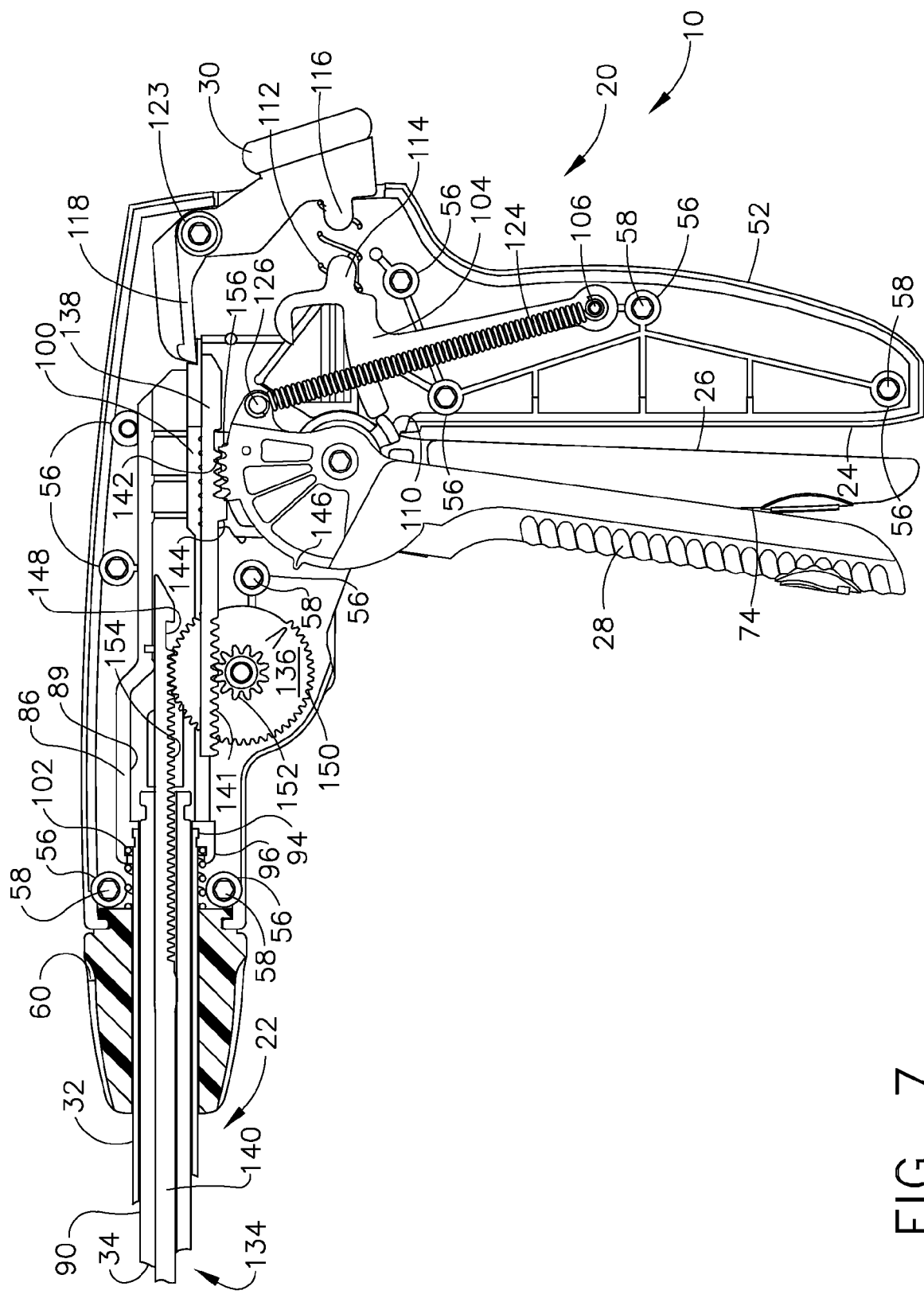
FIG. 7 depicts a side elevational view of the handle portion of proximal end of surgical cutting and stapling instrument of FIG. 1 with the left side removed to expose interior parts in the stapled and severed ("fired") position.

FIGS. 4, 6 and 7 depict respectively the handle assembly 20 in the start position (open and unfired), a clamped position (closed and unfired) and a fired position. The firing trigger 28 may be provided with a gear segment section 156. The gear segment section 156 may engage with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 39 may be engaged with the second notch 148 on the drive member 138 such that the metal drive rod 140 is locked in its proximal-most position, as depicted in FIG. 4. When the upper latch arm 118 falls into the recess 122, the upper latch arm 118 disengages with the second notch 148 to permit distal movement of the metal drive rod 140, as depicted in FIG. 7.

Figure 8:
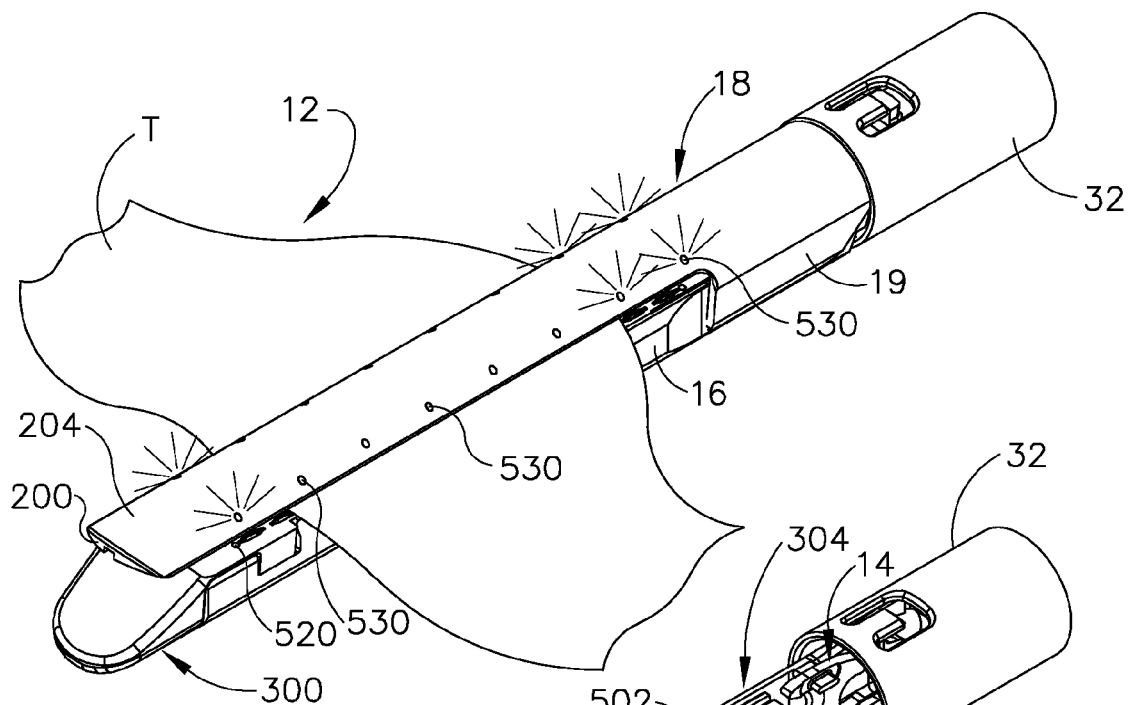
FIG. 8 is a perspective view of an end effector embodiment of FIG. 1 of the present invention clamping a portion of tissue "T" between the anvil and the staple cartridge thereof.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 7. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied. It will be appreciated that the handle assembly 20 is illustrative and that other actuation mechanisms may be employed. For instance, the closing and firing motions may be generated by automated means.

Figure 9:
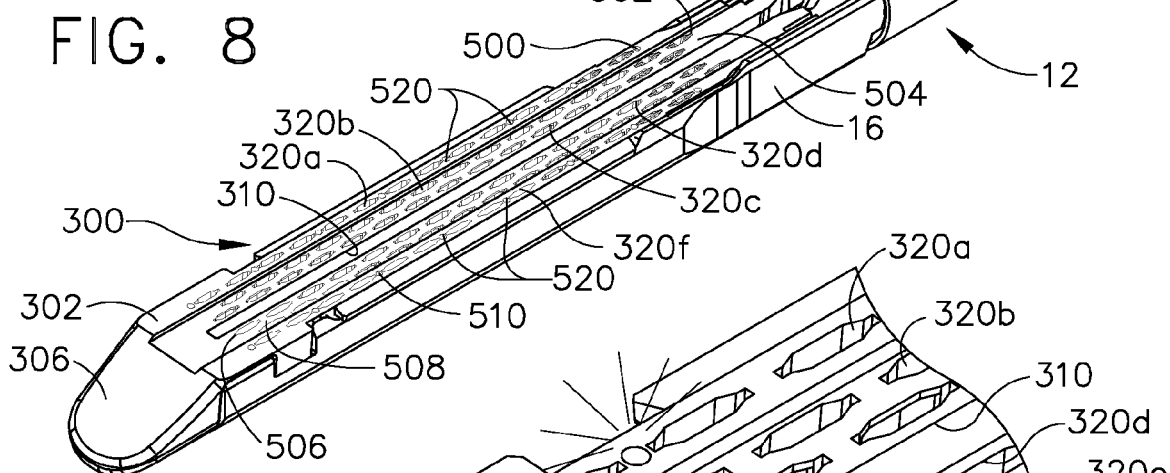
FIG. 9 is a perspective view of the end effector of FIG. 8 with the anvil removed therefrom for clarity.
Figure 10:
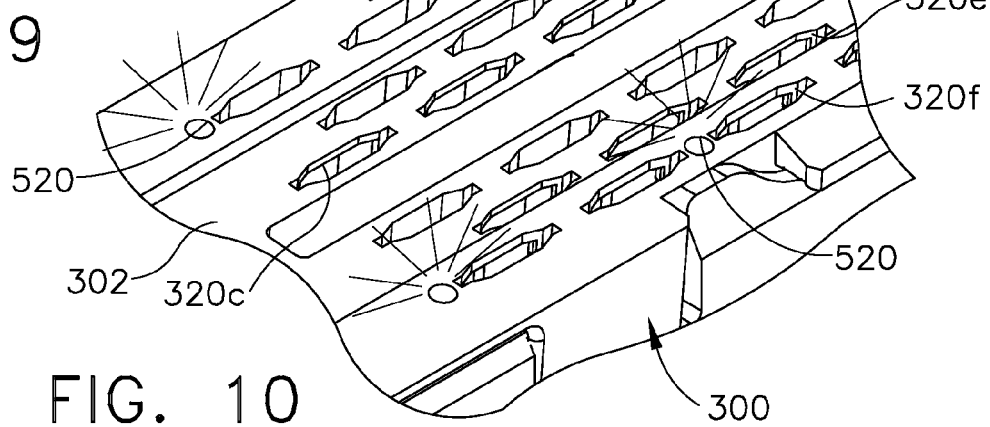
FIG. 10 is a perspective view of a portion of the staple cartridge depicted in FIG. 9.

One embodiment of an end effector 12 of the surgical cutting and stapling instrument 10 is depicted in FIGS. 3 and 8-10. As described above, the handle assembly 20 may produce separate and distinct closing and firing motions that actuate the end effector 12. The end effector 12 may advantageously maintain the clinical flexibility of this separate and distinct closing and firing (i.e., stapling and severing). FIG. 9 depicts a staple cartridge embodiment 300 of the present invention installed in the elongate channel 16 of the end effector 12 with the firing bar 14 in its unfired, proximal position. The staple cartridge 300 has a cartridge body 302 that is divided by an elongate slot 310 that extends from a proximal end 304 of the cartridge 300 towards a tapered outer tip 306. A plurality of staple-receiving channels 320a-320f are formed within the staple cartridge body 302. In various embodiments for example, the staple-receiving channels 320a-320f may be arranged in six laterally spaced longitudinal rows with three rows on each side of the elongated slot 310. Positioned within the staple-receiving channels 320a-320f are the staples 222 (FIG. 3) which may be supported on movable drivers 330 as is known. For example, staple driver arrangements such as those described in co-owned U.S. Patent Application Publication No. 2007/0045379, entitled "Staple Cartridges For Forming Staples Having Differing Formed Staple Heights", the disclosure of which is hereby incorporated by reference in its entirety may be employed. However, other types of staples and staple driver arrangements may be effectively employed without departing from the spirit and scope of the present invention.

The anvil 18 may be movably attached to the proximal end of the elongate channel 16 in a variety of known arrangements such that, as opening and closing motions are applied to the anvil 18, by for example, the closure sleeve 32, the anvil 18 is caused to move between opened and closed positions. The anvil 18 may have a body portion 200 that has a staple forming surface 202 that has a plurality of staple forming pockets therein (not shown) that coincide with the staple channels 320a, 320b, 320c, 320d, 320e, and 320f provided in the staple cartridge 300. The anvil also has a top or outer surface 204. For example, the anvil 18 may be pivotally coupled to the proximal end of the elongate channel by trunnions 232 journaled in slots 230 in the proximal end of the elongate channel 16 (FIG. 11) such that when in the opened position, the staple forming surface 202 of the anvil 18 is spaced away from a staple cartridge 300 mounted within the elongate channel 16 and when a closing motion is applied to the anvil 28 by the closure sleeve 32, the staple forming surface 202 of the anvil 18 is brought into confronting relationship with the staple cartridge 300 to enable tissue "T" to be clamped therebetween as shown in FIG. 8. However the anvil 18 may be movably supported relative to the staple cartridge 300 using a variety of different known anvil attachment arrangements.

Figure 11:
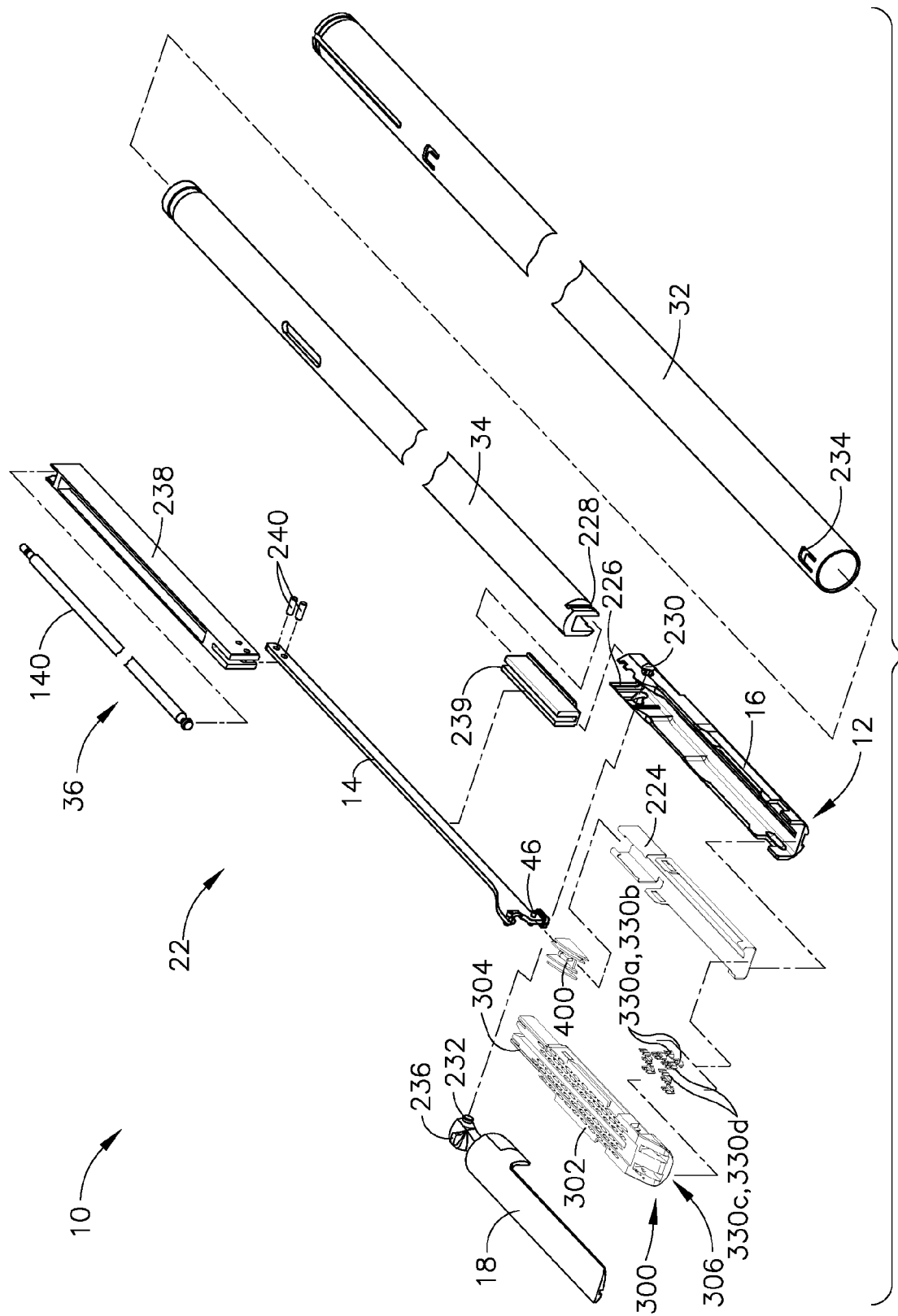
FIG. 11 is an isometric exploded view of the implement portion of the surgical cutting and stapling instrument of FIG. 1.

As can be seen in FIGS. 3 and 11, the cartridge body 302 may be mounted within a cartridge tray 224. As illustrated in FIG. 3, the cartridge body 302 may be formed with two inside longitudinally extending slots 390 and two outside longitudinally extending slots 392. Slots 390 and 392 extend from the proximal end 304 of the cartridge to its tapered outer tip 306. This cartridge embodiment 300 may further include a wedge sled 400 that is slidably supported on the cartridge tray 224. One wedge sled embodiment 400 includes a pair of inside sled cams 410, wherein one inside sled cam 410 corresponds to one of the inside longitudinally extending slots 390 and wherein the other inside sled cam 410 corresponds to the other inside longitudinally extending slot 390. See FIG. 3. The wedge sled 400 may further include a pair of outside sled cams 420, wherein one outside sled cam 420 corresponds to one of the outside longitudinally extending slots 392 and the other outside sled cam 420 corresponds to the other outside longitudinally extending slot 392 as shown in FIG. 19. When assembled, the cartridge tray 224 holds the wedge sled 400 and the drivers 330 inside the cartridge body 302.

As can be seen in FIG. 11, the elongate channel 16 may have a proximally placed attachment cavity 226 for receiving a channel anchoring member 228 on the distal end of the frame 34 for attaching the end effector 12 to the handle assembly 20. The closure sleeve 32 that may encompass the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Returning to FIGS. 3 and 8-10, in various embodiments of the present invention, at least one, and preferably a plurality of light sources 500 are supported within the elongate channel 16. In one embodiment, for example, the light sources 500 may comprise light emitting diodes (LED's) that are in electrical communication with a source of electrical energy 600 mounted within the handle assembly 20 (FIG. 1) by conductors 602 that extend through the elongate channel 16 and the frame 34. In various embodiments, for example, the source of electrical energy may comprise one or more batteries. In still other embodiments, however, the light sources 500 may be powered by alternating current (AC). More particularly, the handle assembly 20 maybe equipped with a power cord (not shown) that may be plugged into an AC outlet. In still other embodiments, the source of electrical energy may comprise one or more batteries operably supported within the frame 34.

As can be seen in FIG. 3, each light source 500 may be mounted within a light-receiving port 510 provided in the elongate channel 16. The cartridge tray 224 and the cartridge body 302 may be provided with light-receiving openings or passages 228, 520, respectively, that correspond to each light source 500 to thereby permit light emitted by each light source 500 to pass through the light-receiving passageways 228, 520 through the cartridge body 302 vertically. Thus, when the clinician is initially grasping moving and manipulating tissue "T" prior to clamping the tissue therein, the light passing through the cartridge body 302 may assist in lighting the area and surrounding tissue.

As can be most particularly seen in FIGS. 3 and 8, however, various embodiments of the present invention may also have light-receiving passages 530 that extend through the anvil body 200. Each light-receiving passage 530 corresponds to a light-receiving passage 520 in the cartridge body 302 such that, when the anvil 18 is in the closed position as shown in FIG. 3, the light will pass from the light-receiving passages 520 in the cartridge body 302 through the corresponding light receiving passages 530 in the anvil body 200. Thus, when the clinician clamps the tissue "T" between the anvil 18 and the cartridge 300 as seen in FIG. 8, those light-receiving passages 228, 520 that are blocked by the tissue "T" will not receive light from their corresponding light source 500. However, light will pass through those passages 228, 520, 530 that are not blocked by the tissue "T". Thus, the clinician will be able to ascertain the position of the tissue "T" that is clamped in the end effector 12 by noting which passages 530 are emitting light. In various embodiments, the anvil 18 may also be equipped with at least one, and preferably two, downwardly extending tissue locators 19 that serve to help position the tissue "T" within the end effector 12.

Figure 12:
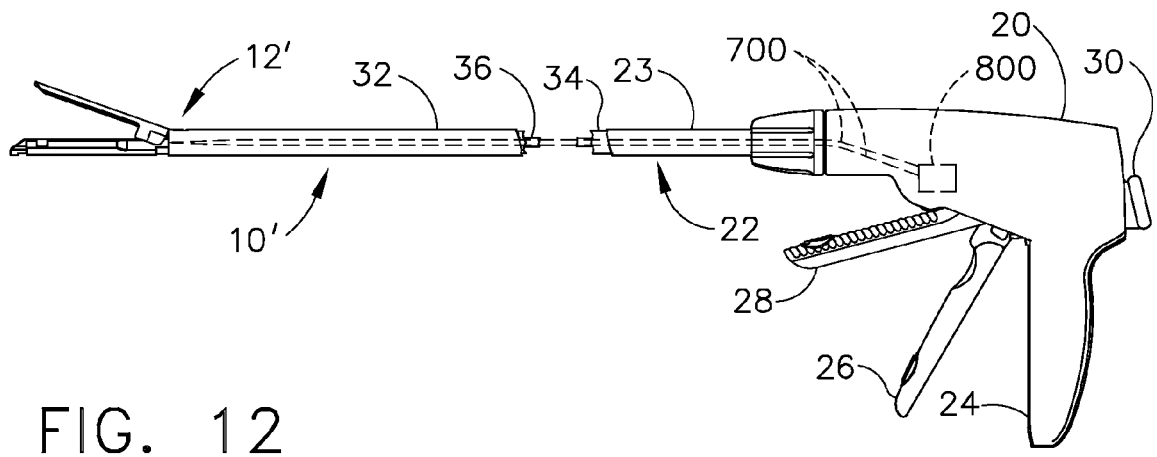
FIG. 12 depicts a partially cut away side elevation view of a surgical cutting and stapling instrument of another embodiment of the present invention in an open position.
Figure 13:
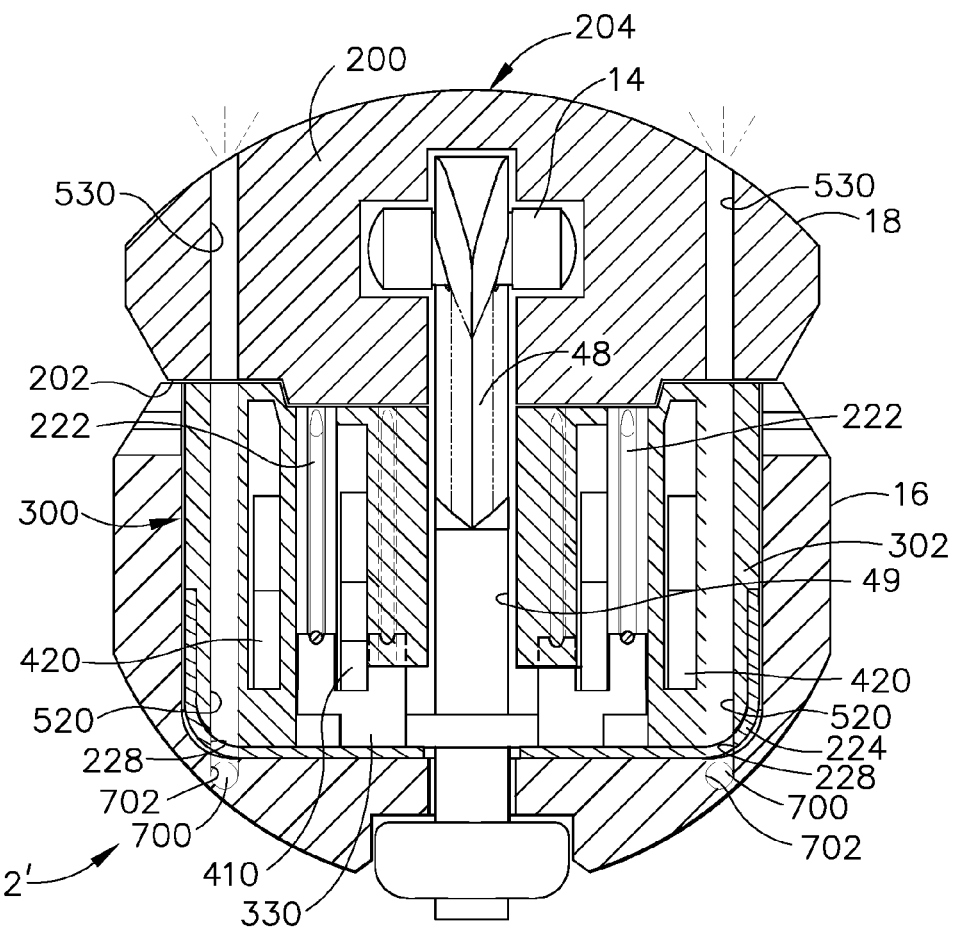
FIG. 13 is a cross-sectional view of the end effector of FIG. 12 with the anvil thereof in a closed position.

FIGS. 12 and 13 illustrate an alternative surgical cutting and stapling instrument 10' that has an alternative end effector embodiment 12' that may be substantially identical to the end effector 12 described above, except for the differences discussed below. For example, in this end effector embodiment 12', at least one, and preferably at least two, fiber optic cables 700 are mounted within channels 702 provided in the elongate channel 16 as shown in FIG. 13. The fiber optic cables 700 may cooperate with at least one source of light 800 mounted in the handle assembly 20 or in the frame 34. The at least one source of light 800 may comprise one or more light emitting diodes, etc. The fiber optic cables 700 serve to communicate the light being emitted from the light source 800 into the corresponding light-receiving passageways 228 in the tray cartridge 224 and the light-receiving passages 520 in the cartridge body 302 for discharge through the light-receiving passageways 530 in the anvil body 200.

FIGS. 14-17 illustrate another alternative end effector embodiment 12" that may be substantially identical to the end effector 12 described above, except for the differences discussed below. For example, in this end effector embodiment 12", a plurality of light sources 800 are mounted in the staple cartridge body 302. In various embodiments, the light sources 800 comprise light emitting diodes that are electrically coupled by corresponding conductors 802 to contacts 804 mounted in the bottom surface of the cartridge body 302 and extending through the cartridge tray 224. See FIG. 17. When the staple cartridge 300 is installed within the elongate channel 16, the first contacts are retained in electrical contact with corresponding second contacts mounted in the elongate channel 16 and in electrical contact with a source of electrical energy such as, for example, a battery or batteries mounted in the frame 34 or the handle assembly 20. Thus, when the cartridge 300 is installed in the elongate channel 300, the light sources 800 are powered by virtue of electrical interconnection between the corresponding first and second contacts 804, 806.

In the various end effector embodiments disclosed herein, light emitting diodes of differing colors may be employed, for example, to differentiate between different portions of the end effector to further assist the clinician in determining the position of the tissue within the end effector. For example, the distal end portion of the end effector may be equipped with red lights. The central portion of the end effector may have green lights and the proximal end portion may have yellow lights, etc.

Figure 14:
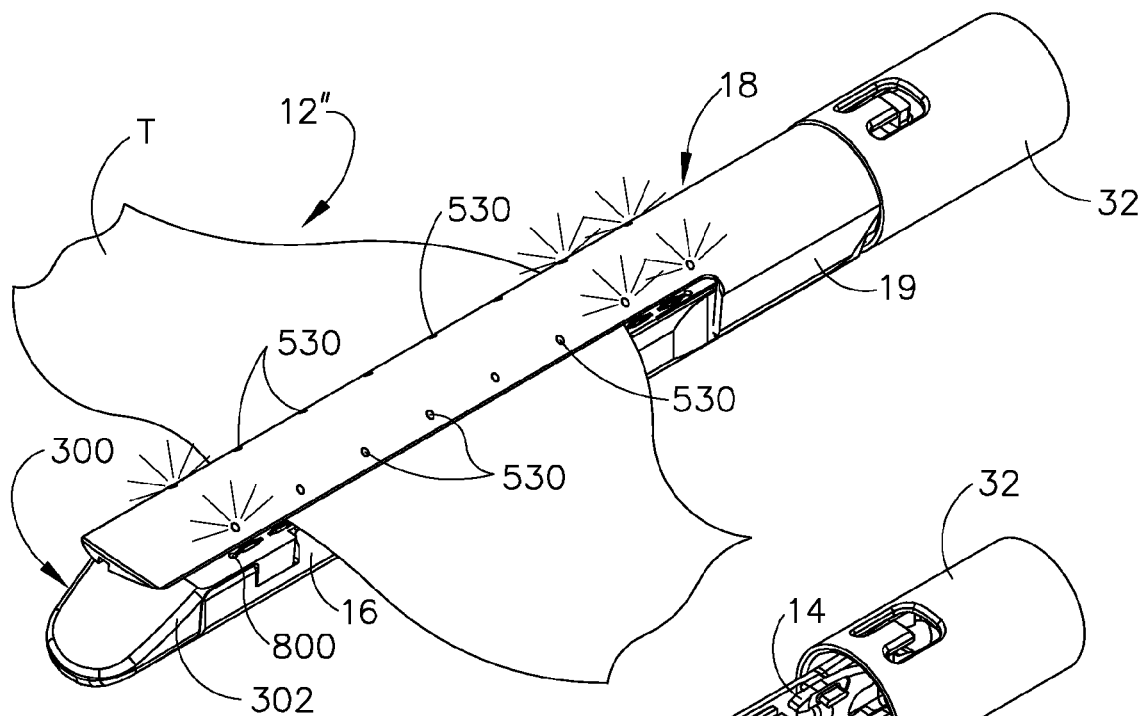
FIG. 14 is a perspective view of another end effector embodiment of the present invention clamping a portion of tissue "T" between the anvil and the staple cartridge thereof.
Figure 15:
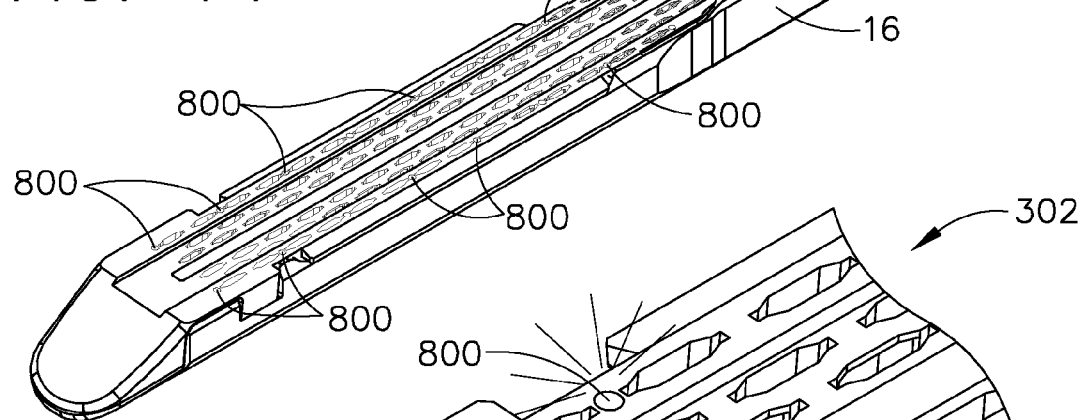
FIG. 15 is a perspective view of the end effector of FIG. 14 with the anvil removed therefrom for clarity.
Figure 16:
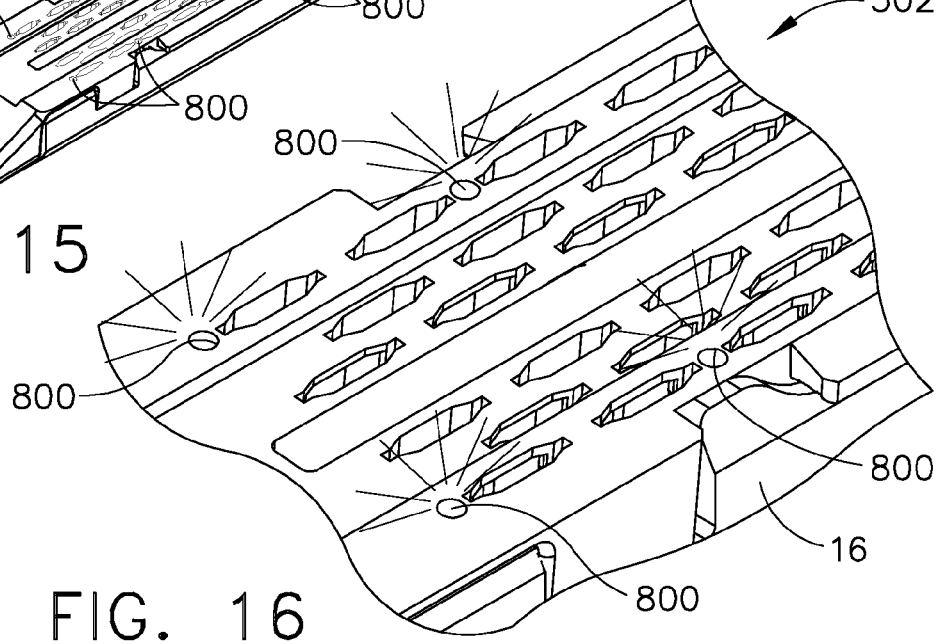
FIG. 16 is a perspective view of a portion of the staple cartridge depicted in FIG. 15.
Figure 17:
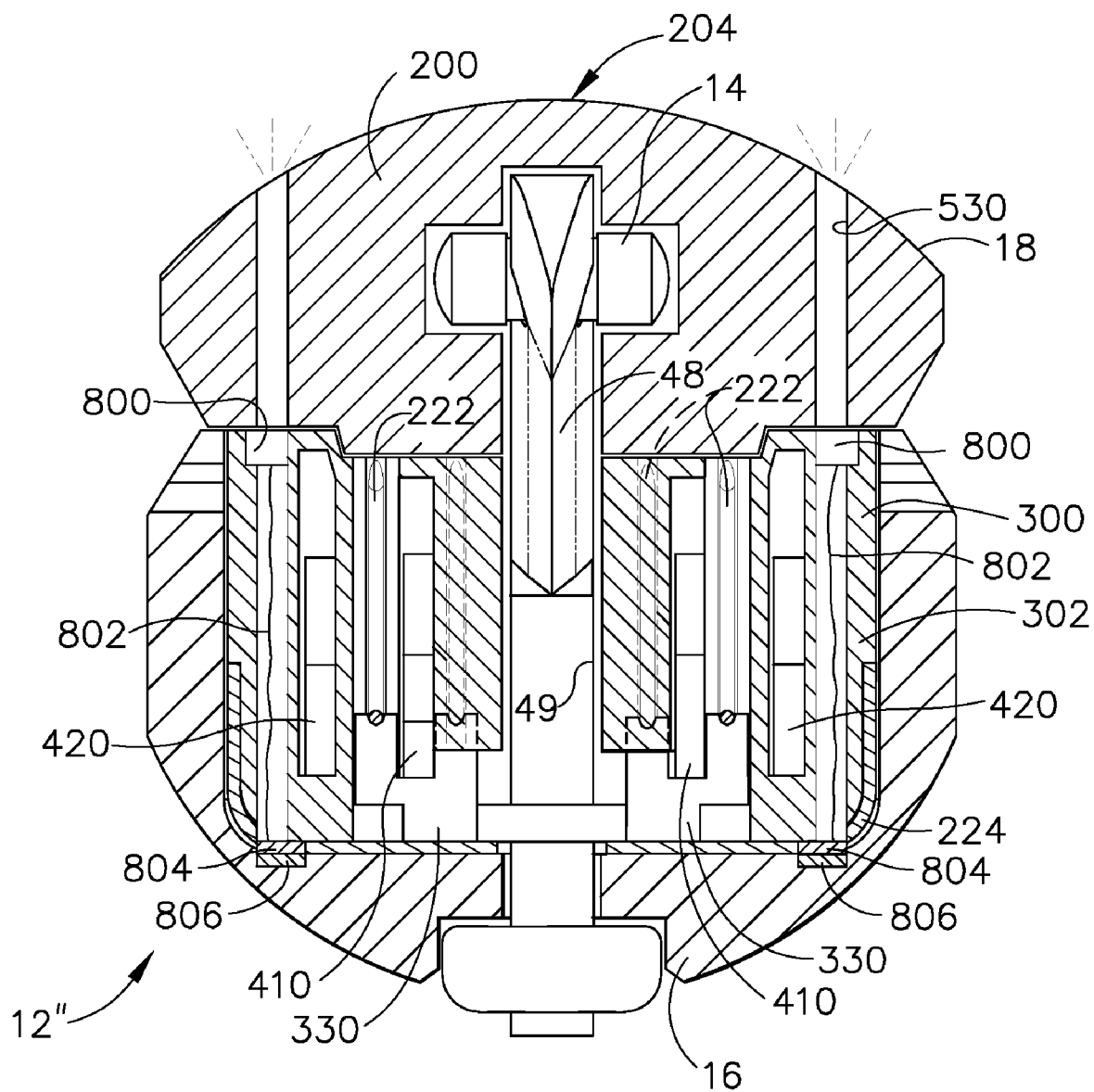
FIG. 17 is a cross-sectional view of the end effector of FIGS. 14-16 with the anvil thereof in a closed position.

In use, the surgical stapling and severing instrument 10 is used as depicted in FIGS. 1-2. In FIGS. 1-2, the instrument 10 is in its start position, having had an unfired, fully loaded staple cartridge 300 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue "T" to be stapled and severed is positioned between the staple cartridge 300 and the anvil 18, as depicted in FIGS. 8 and 14. The clinician then moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the firing bar 14 is aligned for firing through the end effector 12. After tissue clamping has occurred, the clinician moves the firing trigger 28 proximally causing the firing bar 14 to move distally into the end effector 12. The clinician continues moving the firing trigger 28 until brought proximal to the closure trigger 26 and pistol grip 24. Thereby, all of the ends of the staples 222 are bent over as a result of their engagement with the anvil 18. The cutting edge 48 has traversed completely through the tissue. The process is complete by releasing the firing trigger 28 and by then depressing the release button 30 while simultaneously squeezing the closure trigger 26 to open the end effector 12.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior end effectors.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various end effector embodiments of the present invention may find utility when used in connection with other forms of end effectors and stapling apparatuses without departing from the spirit and scope of the present invention. For example, the various unique and novel features of the various embodiments of the present invention may be effectively employed with other forms of tissue grasping and tissue manipulating end effectors. Thus, as used herein, the term "end effector" should not be limited to cutting and stapling end effectors. In addition, various end effectors disclosed herein are designed to be used with a reusable firing bar/knife arrangement that comprises a part of the surgical cutting and stapling instrument and which is not disposed of with the spent staple cartridge. Those of ordinary skill in the art will appreciate, however, that the unique and novel advantages and features of the various embodiments of the present invention may also be effectively employed in connection with end effectors known in the art as "disposable loading units"—or units, for example, wherein the knife bar is disposed of with the spent staple cartridge. Accordingly, the term "end effector" as used herein is also intended to encompass such disposable loading units as well.

Moreover, the devices disclosed herein can be designed to be disposed of after a single use, or they can be designed to be used multiple times. In either case, however, the device may be reconditioned for reuse after at least one use. Reconditioning may include any combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical cutting and stapling instrument comprising:
a handle assembly;
an elongate shaft operably coupled to said handle assembly;
an elongate channel operably coupled to said elongate shaft and configured to operably support a staple cartridge therein;
an anvil movably supported relative to said elongate channel for selective movement between an open position and a closed position wherein tissue is clamped between said anvil and a staple cartridge supported within said elongate channel in response to opening and closing motions applied thereto from the elongate shaft;
a plurality of electrical powered light sources in the staple cartridge; and
at least one electrical contact supported in said elongate channel and in electrical communication with a source of electrical energy such that when the staple cartridge is operably supported within said elongate channel, said at least one electrical contact electrically interfaces with a corresponding at least one electrical contact in the staple cartridge to transmit electrical power to the plurality of light sources therein and wherein said plurality of electrical powered light sources interface with said anvil to provide a visual indication viewable through a portion of said anvil to indicate a position of tissue clamped between said anvil and the staple cartridge.

2. The surgical cutting and stapling apparatus of claim 1 wherein said plurality of electrical powered light sources comprises a plurality of light emitting diodes.

3. The surgical cutting and stapling apparatus of claim 2 wherein said plurality of light emitting diodes are provided in at least two different colors.

4. The end effector of claim 1 wherein said anvil has at least one tissue locator thereon.

* * * * *